(12) United States Patent
Sun et al.

(10) Patent No.: US 7,485,471 B1
(45) Date of Patent: Feb. 3, 2009

(54) DETECTION OF ENHANCED MULTIPLEX SIGNALS BY SURFACE ENHANCED RAMAN SPECTROSCOPY

(75) Inventors: Lei Sun, Santa Clara, CA (US); Xing Su, Cupertino, CA (US)

(73) Assignee: Intel Corporation, Santa Clara, CA (US)

( * ) Notice: Subject to any disclaimer, the term of this patent is extended or adjusted under 35 U.S.C. 154(b) by 568 days.

(21) Appl. No.: 11/016,613

(22) Filed: Dec. 17, 2004

(51) Int. Cl.
*G01N 33/553* (2006.01)

(52) U.S. Cl. ............... 436/525; 436/518; 436/524; 435/283.1; 435/287.2; 435/288.7; 435/288.1; 435/288.3; 359/326; 359/327

(58) Field of Classification Search .......... 436/518, 436/524, 525; 435/283.1, 287.2, 288.7, 288.1, 435/288.3; 359/326, 327
See application file for complete search history.

(56) References Cited

U.S. PATENT DOCUMENTS

| | | | |
|---|---|---|---|
| 5,266,498 A * | 11/1993 | Tarcha et al. | 436/525 |
| 5,306,403 A | 4/1994 | Vo-Dinh | |
| 5,567,628 A | 10/1996 | Tarcha et al. | |
| 6,002,471 A | 12/1999 | Quake | |
| 6,174,677 B1 | 1/2001 | Vo-Dinh | |
| 7,267,948 B2 * | 9/2007 | Vo-Dinh | 435/6 |
| 2002/0132371 A1 * | 9/2002 | Kreimer et al. | 436/525 |
| 2002/0137058 A1 * | 9/2002 | Mirkin et al. | 435/6 |
| 2003/0211488 A1 | 11/2003 | Mirkin et al. | |
| 2005/0147976 A1 * | 7/2005 | Su | 435/6 |
| 2006/0147927 A1 * | 7/2006 | Geddes et al. | 435/6 |

FOREIGN PATENT DOCUMENTS

| | | |
|---|---|---|
| WO | WO-02/096262 | 12/2002 |
| WO | WO-2005/066373 | 7/2005 |
| WO | WO-2005/098441 | 10/2005 |

OTHER PUBLICATIONS

Borrebaeck, Carl A.K. ed. (1995). *Breakthroughs in Molecular Biology: Antibody Engineering.* Oxford University Press: New York City, NY. pp. ii-xi Table of Contents.
Cao et al. (2002). "Nanoparticles with Raman Spectroscopic Fingerprints for DNA and RNA Detection," *Science* 297:1536-1540.
Ecker and Crooke. (1995). "Combinatorial Drug Discovery: Which Methods Will Produce the Greatest Value?," *BioTechnology* 13 351-360.
Grubisha et al. (2003). "Femtomolar Detection of Prostate-Specific Antigen: An immunoassay Based on Surface-Enhanced Raman Scattering and Immunogold Labels," *Analytical Chemistry* 75(21): 5936-5943.
Harlow and Lane. (1998). *Antibodies: A Laboratory Manual* Cold Spring Harbor Laboratory: Cold Spring Harbor, NY, pp. iii-ix Table of Contents.

(Continued)

*Primary Examiner*—Long V. Le
*Assistant Examiner*—Melanie J. Yu
(74) *Attorney, Agent, or Firm*—Darby & Darby, P.C.

(57) ABSTRACT

Various methods of using Raman-active or SERS-active probe constructs to detect analytes in biological samples, such as the nucleic acid and/or protein-containing analytes in a body fluid are provided.

26 Claims, 4 Drawing Sheets

OTHER PUBLICATIONS

Hilyard et al. (1992). "Protein engineering of antibody combining sites" Chapter in *Protein Engineering: A Practical Approach*. Rees, Sternberg, and Wetzel, eds., IRL Press at Oxford University Press: New York, NY, pp. 253-275.

Huse et al. (1989). "Generation of a Large Combinatorial Library of the Immunoglobulin Repertoire in Phage Lambda," *Science* 246: 1275-1281.

Jellinek et al. (1995). "Potent 2'-Amino-2'-deoxypyrimidine RNA Inhibitors of Basic Fibroblast Growth Factor," *Biochemistry* 34:11363-11372.

Lerner, Michael R. (1994). "Tools for investigating functional interactions between ligands and G-Protein-coupled receptors," *TINS* 17(4):142-146.

Lin et al. (1994). "Modified RNA sequence pools for in vitro selection," *Nucleic Acids Research* 22(24): 5229-5234.

Pagratis et al. (1997). "Potent 2'-amino, and 2'-fluro-2'deoxyribonucleotide RNA inhibitors of keratinocyte growth factor," *Nature Biotechnology* 15:68-73.

Sambrook et al. (1989). *Molecular Cloning: A Laboratory Manual*. Cold Springs Harbor Laboratory Press: Cold Springs Harbor, NY, pp. xi-xxxviii Table of Contents.

Tam et al. (1994). "Biological availability and nuclease resistance extend the in vitro activity of a phosphorothioate-3'hydroxypropylamine oligonucleotide," *Nucleic Acids Research* 22(6): 977-986.

Ward et al. (1989). "Binding activities of a repertoire of single immunoglobulin variable domains secreted from *Escherichia coli*," *Nature* 341:544-546.

Winter and Harris. (1993). "Humanized antibodies." *Immunology Today* 14(6): 243-246.

\* cited by examiner

FIG. 1A Improved Method

FIG. 1B Previous Method

DETECTION OF ENHANCED MULTIPLEX SIGNALS BY SURFACE ENHANCED RAMAN SPECTROSCOPY

BACKGROUND OF THE INVENTION

1. Field of the Invention

The present invention relates generally to methods and devices useful to identify the presence of an analyte in a sample.

2. Background Information

Surface-enhanced Raman scattering (SERS) is a sensitive spectroscopic method for detection of an analyte. Raman Spectroscopy probes vibrationally excitable levels of an analyte. Once a vibrational level is excited by a photon, the energy of the photon shifts by an amount equal to that of the level (Raman scattering). A Raman spectrum, similar to an infrared spectrum, consists of a wavelength distribution of bands corresponding to molecular vibrations specific to the sample being analyzed (the analyte). In the practice of Raman spectroscopy, the beam from a radiation source is focused upon the sample to thereby generate inelastically scattered radiation, which is optically collected and directed into a wavelength-dispersive spectrometer in which a detector converts the energy of impinging photons to electrical signal intensity. In SERS, analyte molecules are adsorbed on noble metal nanoparticles. These nanoparticles, once excited by light, set up plasmon modes, which, in turn, create near fields around each particle. These fields can couple to analyte molecules in the near field regions. As a result, concentration of the incident light occurs at close vicinity of the nanoparticles enhancing the Raman scattering from the analyte molecules. This method can enhance the detection of biological systems by as much as a factor of $10^{14}$.

Multiplexing is a demanding approach for high throughput assays in various areas such as biological research, clinical diagnosis and drug screening because of its great potentials in increasing efficiencies of chemical and biochemical analyses. In a multiplex assay, multiple probes are used that have specificities to corresponding analytes in a sample mixture. One of the critical challenges in establishing a multiplex platform is to develop a probe identification system that has distinguishable components for each individual probe in a large probe set.

Previous methods have utilized SERS in combination with multiplex analysis. Such methods utilize target-coated gold particles and DNA probes co-modified with both a Raman dye and thiol group (Cao et al, *Science* 297: 1536). However, such reagents are generally expensive to manufacture and labor intensive to use. In addition, coupling the Raman dye and thiol group to the analyte does not provide flexibility in application and/or removal of the dye or SERS substrate. Thus, there exists a need for compositions and methods that provide lower costs and increased flexibility in labeling analytes and capture reagents during multiplex analysis.

The following detailed description contains numerous specific details in order to provide a more thorough understanding of the disclosed embodiments of the invention. However, it will be apparent to those skilled in the art that the embodiments can be practiced without these specific details. In other instances, devices, methods, procedures, and individual components that are well known in the art have not been described in detail herein.

DETAILED DESCRIPTION OF THE INVENTION

Figure 1:
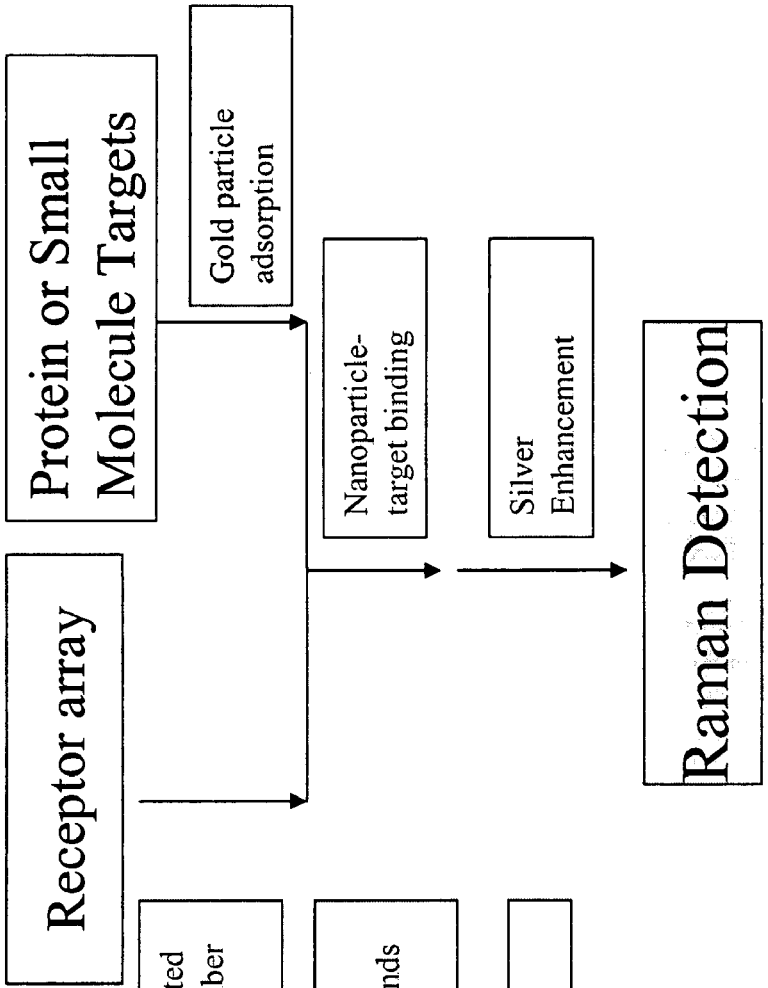
FIG. 1A is a schematic flow chart illustrating an improved method for detection of an analyte. Capture reagents bound to a solid support (e.g., antibodies) include a Raman label. The binding of a target analyte is subsequently detected by Raman detection.
FIG. 1B is a schematic flow chart illustrating previous methods for detection of an analyte absent interchangeable binding members and Raman labeled capture reagents.
Figure 3:
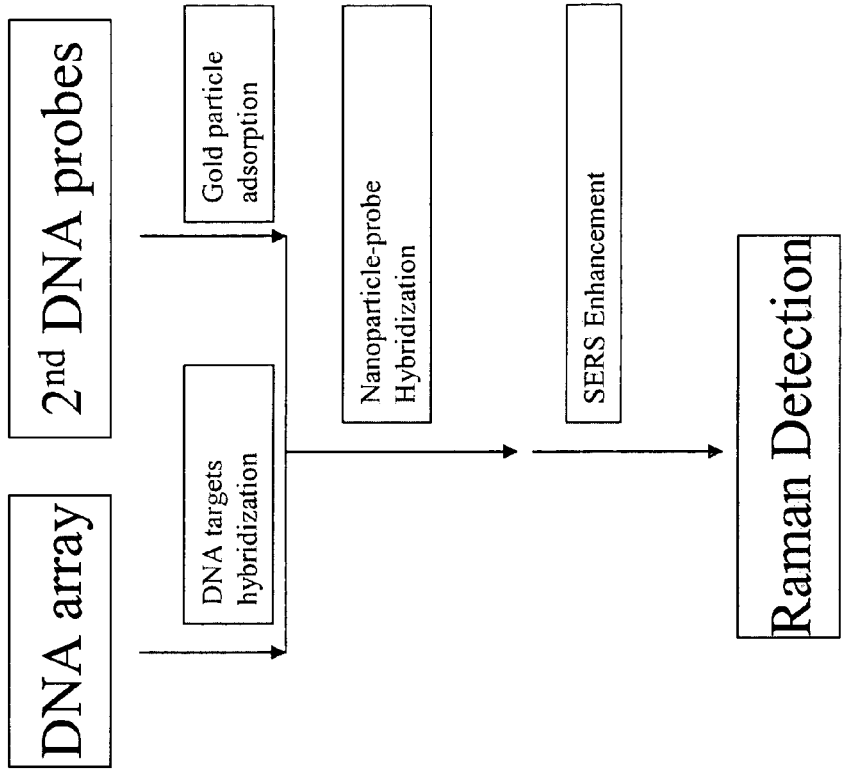
FIG. 3A is a schematic flow chart illustrating an improved method for detection of a nucleic acid sequence (e.g., SNP). Capture nucleic acids bound to a solid support include hybridize a target nucleic acid associated with a first binding member. Hybridization of the target nucleic acid is subsequently detected by Raman detection.
FIG. 3B is a schematic flow chart illustrating previous methods for detection of a nucleic acid sequence absent interchangeable binding members.
Figure 4:
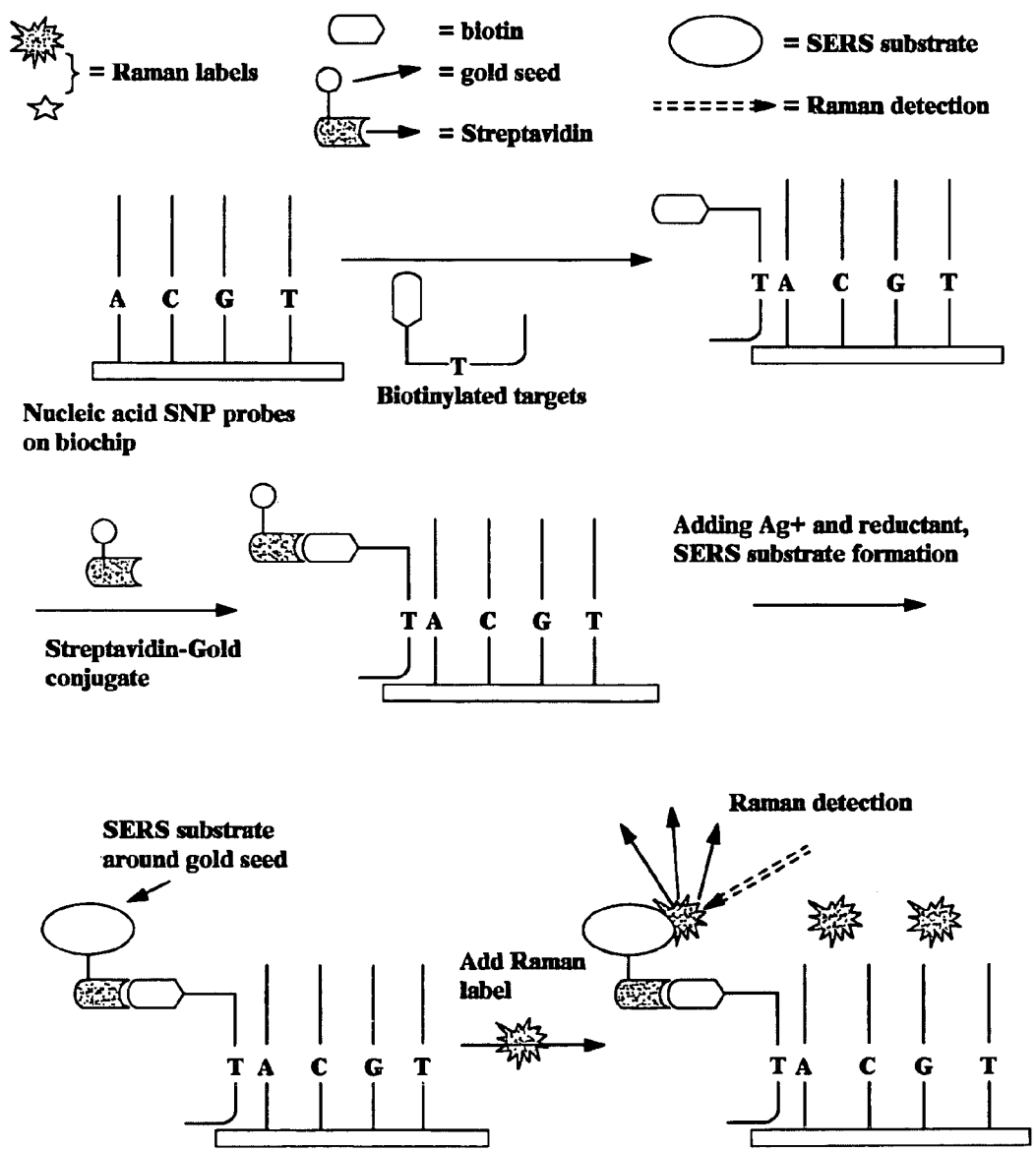
FIG. 4 is a schematic diagram illustrating an improved method for detection of a nucleic acid sequence. The exemplary diagram illustrates target nucleic acids hybridizing to immobilized capture nucleic acid molecules.

The various embodiments of the invention relate to signal amplification methods for multiplex biological assays. In general, biological target complexes are tagged by a seed substance that can catalyze the formation of a surface-enhanced Raman scattering (SERS) substrate. The target complexes can then bind to capture reagents which include a Raman label. The SERS substrate is then generated on the seed substance through reduction of metal cations. The target signals are detected by SERS measurement of the Raman labels. More specifically, embodiments of the invention provide target analytes functionalized with specific binding members comprising seed particles. Embodiments of the invention further relate to target complexes formed between such target analytes and a capture reagent bound to a solid substrate. The capture reagent optionally includes a Raman label. Other embodiments of the invention relate to methods of detecting binding of a target analyte to a capture reagent coupled with surface-enhanced Raman scattering (SERS) spectroscopy, to perform multiplexed detection of analytes. This is exemplified for polypeptide targets in FIGS. 1A, 1B and 2, and for nucleic acid targets in FIGS. 3A, 3B and 4.

Accordingly, in one embodiment, a biological target complex including a target analyte associated with a first specific binding member is provided. The target complex further includes a second specific binding member that binds to the first specific binding member forming a target complex. The second specific binding member includes a seed particle suitable for catalyzing the formation of a surface enhanced Raman scattering (SERS) substrate. Subsequently, the SERS substrate can be activated to provide a SERS effect. The complex further includes a capture reagent bound to a solid substrate. The capture reagent can include a Raman label.

"Target analyte," as used herein, is the substance to be detected in the test sample using the present invention. The analyte can be any substance for which there exists a naturally occurring capture reagent (e.g., an antibody, polypeptide, DNA, RNA, cell, virus, etc.) or for which a capture reagent can be prepared, and the target analyte can bind to one or more capture reagents in an assay. "Target analyte" also includes any antigenic substances, haptens, antibodies, and combinations thereof. The target analyte can include a protein, a peptide, an amino acid, a carbohydrate, a hormone, asteroid, a vitamin, a drug including those administered for therapeutic purposes as well as those administered for illicit purposes, a bacterium, a virus, and metabolites of or antibodies to any of the above substances "Target analyte-analog", as used herein, refers to a substance which cross reacts with an analyte capture reagent although it may do so to a greater or lesser extent than does the target analyte itself. The target analyte-analog can include a modified target analyte as well as a fragmented or synthetic portion of the target analyte molecule so long as the target analyte analog has at least one epitopic site in common with the target analyte of interest.

"Specific binding member," as used herein, is a member of a specific binding pair, i.e., two different molecules where one of the molecules (e.g., a first specific binding member), through chemical or physical means, specifically binds to the second molecule (e.g., a second specific binding member). In addition to antigen and antibody-specific binding pairs, other specific binding pairs include biotin and avidin, carbohydrates and lectins, complementary nucleotide sequences (including probe and captured nucleic acid sequences used in DNA hybridization assays to detect a target nucleic acid sequence), complementary peptide sequences, effector and receptor molecules, enzyme cofactors and enzymes, enzyme inhibitors a and enzymes, cells, viruses and the like. Furthermore, specific binding pairs can include members that are analogs of the original specific binding member. For example a derivative or fragment of the analyte, i.e., an analyte-analog, can be used so long as it has at least one epitope in common with the analyte. Immunoreactive specific binding members include antigens, haptens, antibodies, and complexes thereof including those formed by recombinant DNA methods or peptide synthesis.

"Ancillary Specific binding member," as used herein, is a specific binding member used in addition to the specific binding members of the target analyte and the capture reagent and becomes a part of the final complex. One or more ancillary specific binding members can be used in an assay. "Binding," as used herein, is any process resulting in the formation of coupled moieties. The process of "binding" refers to the direct or indirect attachment of one moiety to another through the formation of at least one bond, which can include covalent, ionic, coordinative, hydrogen, or Van der Waals bonds, or non-chemical interactions, for example, hydrophobic interactions. It is understood that two moieties can be coupled to each other by numerous ways. Such coupling can include, but is not limited to, specific non-covalent affinity interations, for example streptavidin: or avidin:biotin interactions and hapten:antibody interactions; hydrophobic interactions; magnetic interactions; polar interactions, for example, "wetting" associations between two polar surfaces or between oligonucleotide/polyethylene glycol; formation of a covalent bond, for example, an amide bond, a disulfide bond, a thio-ether bond, an ether bond, a carbon-carbon bond; or via other crosslinking agents; or via an acid-labile linker. Exemplary coupled moieties include, but are not limited to, antibody-epitope complexes, receptor-ligand complexes or complementary nucleic acid complexes. Exemplary target analyte-capture reagent complexes include a target nucleic acid sequence (i.e., a target analyte) hybridizing to a complementary nucleic acid sequence (i.e. a capture reagent). Other exemplary target analyte-capture reagent complexes include a target polypeptide (i.e., a target analyte) binding to a receptor or antibody (i.e. a capture reagent), thus forming a ligand binding pair. The extent of the binding is influenced by the presence, and the amount present, of the target analyte. "Associated," as used herein, is the state of two or more molecules and/or particulates being held in close proximity to one another.

"Capture reagent," as used herein, is a molecule or compound capable of binding the target analyte or target reagent, which can be directly or indirectly attached to a substantially solid material. The capture agent can be any substance for which there exists a naturally occurring target analyte (e.g., an antibody, polypeptide, DNA, RNA, cell, virus, etc.) or for which a target analyte can be prepared, and the capture reagent can bind to one or more target analytes in an assay.

"Seed particle," as used herein, is any substance that can precipitate formation of a nanoparticle from a metal colloid solution and support the phenomenon of a surface-enhanced Raman light scattering (SERS) or surface-enhanced resonance Raman light scattering (SERRS). Examples of seed particles include, but are not limited to: Colloids of gold or silver, Pt, Cu, Ag/Au, Pt/Au, Cu/Au, coreshell or alloy particles; particles or flakes of gold, silver, copper, or other substances displaying conductance band electrons. As the particle surface participates in the SERS and SERRS effect, flakes or particles of substances not displaying conductance band electrons, which have been coated with a substance which does, also become suitable particulates.

"Raman label," as used herein, is any substance which produces a detectable Raman spectrum, which is distinguishable from the Raman spectra of other components present, when illuminated with a radiation of the proper wavelength. Other terms for a Raman label include "Raman-active label," "Raman dye" and "Raman reporter molecule." A Raman label includes any organic or inorganic molecule, atom, complex or structure, including but not limited to synthetic molecules, dyes, naturally occurring pigments such as phycoerythrin, organic nanostructures such as C60, buckyballs and carbon nanotubes, metal nanostructures such as gold or silver nanoparticles or nanoprisms and nano-scale semiconductors such as quantum dots. Numerous examples of Raman labels are disclosed below. Exemplary Raman labels are provided in Table 1 below. The skilled artisan will realize that such examples are not limiting, and that "Raman label" encompasses any organic or inorganic atom, molecule, compound or structure known in the art that can be detected by Raman spectroscopy. A particular type of "Raman label" includes "Raman dyes." Examples of Raman dyes include chemical labels such as cresyl fast violet (CFV, Fluka), brilliant cresyl blue (BCB, Allied Chemical and Dye) and p-aminobenzoic acid (PABA, Aldrich). Additional dyes include Cy3, Cy3.5, Cy5, TAMRA (TMR), Texas-Red (TR) and Rhodamine 6G (RD).

Raman labels offer the advantage of producing sharp spectral peaks, allowing a greater number of distinguishable labels to be attached to probes. Additional non-limiting examples of Raman-active labels of use include TRIT (tetramethyl rhodamine isothiol), NBD (7-nitrobenz-2-oxa-1,3-diazole), Texas Red dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, TET (6-carboxy-2',4,7,7'-tetrachlorofluorescein), HEX (6-carboxy-2',4,4',5',7,7'-hexachlorofluorescein), Joe (6-carboxy-4',5'-dichloro-2',7'-dimethoxyfluorescein) 5-carboxy-2',4',5',7'-tetrachlorofluorescein, 5-carboxyfluorescein, 5-carboxy rhodamine, Tamra (tetramethylrhodamine), 6-carboxyrhodamine, Rox (carboxy-X-rhodamine), R6G (Rhodamine 6G), phthalocyanines, azomethines, cyanines (e.g. Cy3, Cy3.5, Cy5), xanthines, succinylfluoresceins, N,N-diethyl-4-(5'-azobenzotriazolyl)-phenylamine and aminoacridine. These and other Raman-active tags can be obtained from commercial sources (e.g., Molecular Probes, Eugene, Oreg.).

It is contemplated that the Raman-active label may comprise one or more double bonds, for example carbon to nitrogen double bonds. It is also contemplated that the Raman-active labels may comprise a ring structure with side groups attached to the ring structure, such as polycyclic aromatic compounds in general. Compounds with side groups that increase Raman intensity include compounds with conjugated ring structures, such as purines, acridines, Rhodamine dyes and Cyanine dyes. The overall polarity of a polymeric active molecular Raman code is contemplated to be hydrophilic, but hydrophobic side groups can be included. Other tags that can be of use include cyanide, thiol, chlorine, bromine, methyl, phosphorus and sulfur.

Included herein are guidelines useful for designing and manufacturing Raman labels. Briefly, exemplary Raman labels provided herein encompass those that comprise any combination of the following attributes: 1) a conjugated aromatic system (generally two or more rings); 2) one or more nitrogen or sulphur atoms with a lone pair of electrons (for Ag binding), preferably two of such atoms on the same side of the molecule so that they can chelate a metal atom; 3) as few oxygen atoms as possible; 4) few or no free OH groups in proximity to the Ag binding site; and 5) few competing Ag binding modes.

Accordingly, molecules useful for providing metal surface adsorption generally include at least one N or S atoms with a lone pair of electrons (for Ag binding). In some aspects, it is useful to have two of such atoms on the same side of the molecule so that they can chelate metal atoms. Additionally, in other aspects, a positive charge in the molecule, such as $N^+$, $S^+$, or $C^+$, is included.

Generally, silver colloids are stable with a relatively large surface potential (−60 mV or lower); when organic compound molecules are adsorbed on to silver colloid surfaces, the potential (zeta potential) is reduced and thus cause colloid agglutination with the organic compounds as the "glue". The present study has identified compounds with a conjugated aromatic system that can more efficiently induce aggregation of Ag particles. N or S atoms are suitable for stable binding to Ag surface, and a single binding mode anchored by two chelating electron-donor atoms aids in generating strong Raman signals with simple signature. In general, O atoms, especially those from free hydroxyl groups, compete with N and S for Ag surface binding.

Molecules suitable for providing a strong Raman signal generally include those possessing strong absorption of UV-Visible light (conjugated double bonds and aromatic system). Molecules with strong absorption near the Raman excitation wavelength are included because of their resonance effect. Also included are those molecules with vibration modes such as C—N bond stretching, C—C bond stretching, and 6-member ring breath modes in an aromatic system. Also included are those molecules with few O atoms because, generally, C—O, O—H, and C=O bonds do not provide strong Raman signals.

Also provided are chemical structures that impart a unique Raman signature for a Raman label. The Raman shift of a particular mode can be "moved" to either longer wavelength or shorter wavelength based on its chemical structure environment. For example, neighboring electron-withdrawing group (conjugated aromatic ring, CN, etc.) may move the Raman peak to higher wave number, and electron-donating groups (Amine, thiol, etc.) do the opposite. In addition, unique Raman signatures can be imparted to a molecule by avoiding same vibration modes occurring at different parts of the molecule unless they are symmetrical. Such structure gives double peaks or broadened single peak, which generally complicate the Raman signature.

In certain embodiments, the Raman-active labels used in the invention methods and complexes can be independently selected from the group consisting of nucleic acids, nucleotides, nucleotide analogs, base analogs, fluorescent dyes, peptides, amino acids, modified amino acids, organic moieties, quantum dots, carbon nanotubes, fullerenes, metal nanoparticles, electron dense particles and crystalline particles, or a combination of any two or more thereof.

The present invention contemplates the use of any suitable particle having Raman labels and specific binding substances attached thereto that are suitable for use in detection assays. In practicing this invention, however, nanoparticles are preferred. The size, shape and chemical composition of the particles will contribute to the properties of the resulting probe including the DNA barcode. These properties include optical properties, optoelectronic properties, electrochemical properties, electronic properties, stability in various solutions, pore and channel size variation, ability to separate bioactive molecules while acting as a filter, etc. The use of mixtures of particles having different sizes, shapes and/or chemical compositions, as well as the use of nanoparticles having uniform sizes, shapes and chemical composition, are contemplated. Examples of suitable particles include, without limitation, nano- and microsized core particles, aggregate particles, isotropic (such as spherical particles) and anisotropic particles (such as non-spherical rods, tetrahedral, prisms) and core-shell particles such as the ones described in U.S. patent application Ser. No. 10/034,451, filed Dec. 28, 2002 and International application no. PCT/US01/50825, filed Dec. 28, 2002, which are incorporated by reference in their entirety.

Nanoparticles useful in the practice of the invention include metal (e.g. gold, silver, copper and platinum), semiconductor (e.g., CdSe, CdS, and CdS or CdSe coated with ZnS) and magnetic (e.g., ferromagnetite) colloidal materials. Other nanoparticles useful in the practice of the invention include ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs. The size of the nanoparticles is preferably from about 1.4 nm to about 150 nm (mean diameter), more preferably from about 5 to about 50 nm, most preferably from about 10 to about 30 nm. The nanoparticles may also be rods, prisms, cubes, tetrahedra, or core shell particles.

"SERS (Surface-Enhanced Raman Scattering)" means the increase in Raman scattering exhibited by certain molecules in proximity to certain metal surfaces. "SERRS (Surface Enhanced Resonance Raman Scattering)" results when the adsorbate at a SERS active surface is in resonance with the laser excitation wavelength. The resultant enhancement is the product of the resonance and surface enhancement.

"SERS substrate," as used herein, includes a stain such as a silver or gold stain that provides for activating Raman labels on particles to produce a SERS effect. "Stain," as used herein, includes material, e.g., gold, silver, etc., that can be used to produce or enhance a detectable change in any assay described herein. For example, silver staining can be employed with any type of nanoparticles that catalyze the reduction of silver. Thus, gold colloid exposed to a staining solution containing $AgNO_3$ can serve as nucleation sites for the deposition of Ag.

Figure 2:
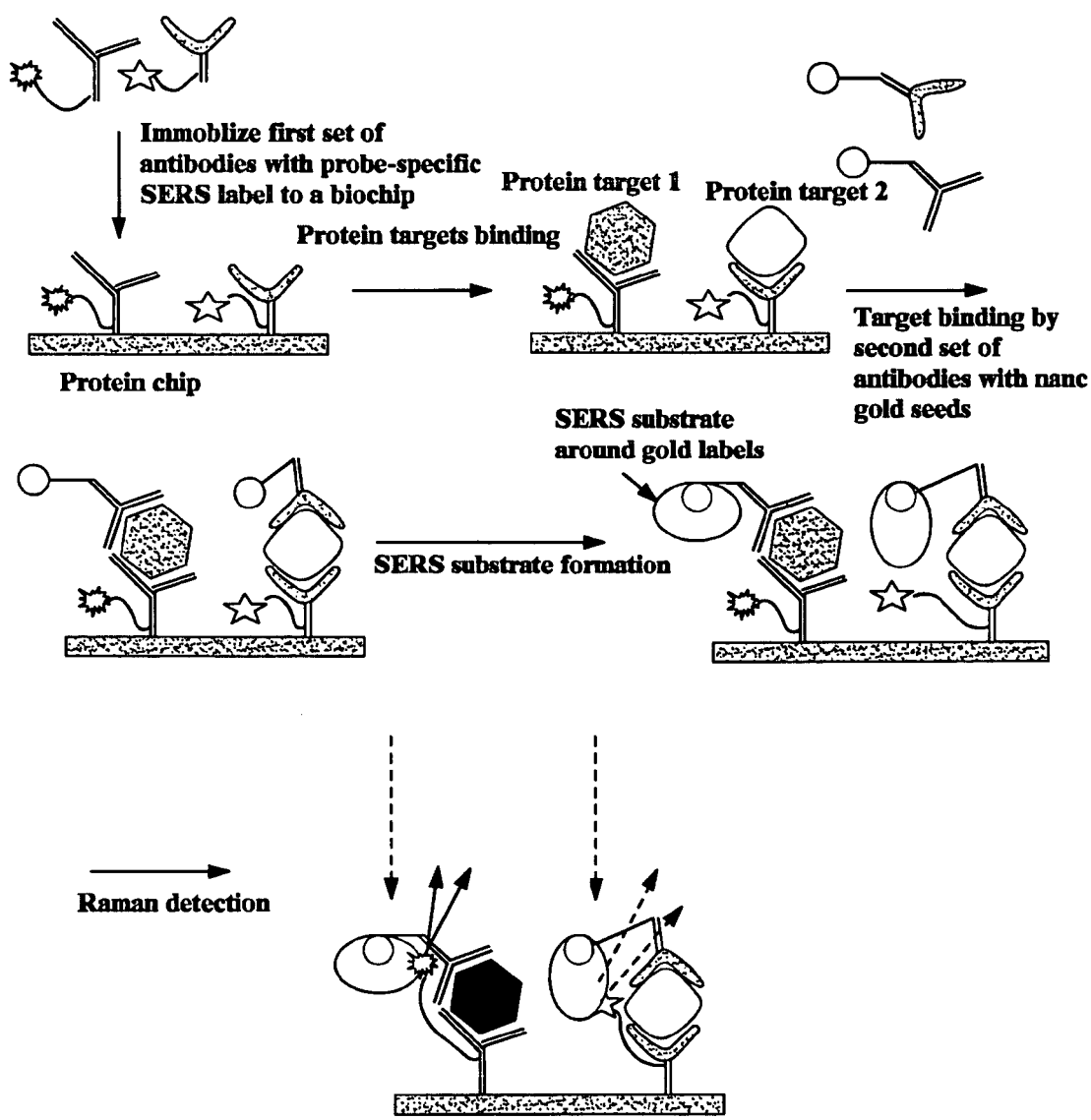
FIG. 2 is a schematic diagram illustrating an improved method for detection of an analyte. The exemplary diagram illustrates protein targets binding to antibodies immobilized to a solid surface and labeled with Raman labels.

"Intermediary molecule," as used herein, is any substance that includes a specific binding member and binds to a target analyte. Exemplary intermediary molecules include antibodies attached to a specific binding member. As shown in FIG. 2, an exemplary intermediary molecule includes second antibody comprising nanogold seeds. Such molecules generally bind to the target analyte following binding of the target analyte to the immobilized capture reagent.

"Radiation," as used herein, is an energy in the form of electromagnetic radiation which, when applied to a test mixture, causes a Raman spectrum to be produced by the Raman-active label therein.

The complexes and methods provided herein are distinguishable from previous reports combining SERS detection with Raman label applications. For example, gold nanoparticles combined with surface-enhanced Raman scattering spectroscopy for detection and identification of single dye molecules has been described by Cao et al (*Science* 297: 1536). Cao et al designed a probe that is built around a 13 nm gold nanoparticle. The nanoparticles are coated with hydrophilic oligonucleotides containing a Raman dye at one end and terminally capped with a small molecule recognition element (e.g. biotin). This molecule is catalytically active and will be coated with silver in the solution of Ag(I) and hydroquinone. After the probe is attached to a small molecule or an antigen it is designed to detect, the substrate is exposed to silver and hydroquinone solution. The silver-plating occurs in close proximity to the Raman dye, which allows for dye signature detection with a standard Raman microscope. In contrast, the complexes disclosed herein are comprised of a Raman dye that is separate from, for example, a gold nanoparticle suitable for supporting a SERS substrate. The biological target complexes comprise a seed particle capable of catalyzing the formation of a SERS substrate. The seed particle is associated with a second binding member which binds to a first binding member associated with a target analyte. Once the target analyte binds to a capture reagent associated with a Raman label the SERS substrate is generated through reduction of metal cations. Alternatively, when a nucleic acid is a the target analyte, the Raman label is added to the SERS substrate subsequent to formation (see e.g., FIGS. 3A, 3B and 4).

Accordingly, in another embodiment, a method for detecting an analyte-capture reagent complex by Raman spectroscopy is provided. The method includes providing a target analyte associated with a first specific binding member and providing a capture reagent bound to a solid substrate. The capture reagent includes a Raman label. The method further includes contacting the target analyte with the capture reagent of under conditions suitable for forming a target analyte-capture reagent complex. The first specific binding partner is contacted with a second specific binding member functionally associated with a seed particle suitable for associating with a SERS substrate. The target analyte-capture reagent complex is then contacted with electromagnetic radiation suitable for detecting a specific property associated with the analyte-capture reagent complex by Raman spectroscopy.

In still another embodiment, the invention provides methods for multiplex detection of analytes in a sample by contacting target analytes in a sample under conditions suitable to form complexes with a set of capture reagents. In the case of a target analyte that is a non-nucleic acid, the capture reagent is conjugated with an Raman label. Each capture reagent can be conjugated to a unique Raman label, such as a Raman dye, associated with a unique optical signature. Following complex formation and SERS activation of the SERS substrate, the unique optical signatures are detected in a multiplex manner with a suitable detection device. Since each specifically binding target analyte is bound to a specific capture reagent conjugated to a known Raman dye that emits a distinguishable optical signature, such as a SERS signal, individual optical signatures detected from the constructs are thus associated with the identity of a tarhet analyte in the sample.

"Test sample," as used herein, means the sample containing the target analyte to be detected and assayed using the present invention. The test sample can contain other components besides the target analyte, can have the physical attributes of a liquid, or a solid, and can be of any size or volume, including for example, a moving stream of liquid. The test sample can contain any substances other than the target analyte as long as the other substances do no interfere with the binding of the target analyte with the capture reagent or the specific binding of the first binding member to the second binding member. Examples of test samples include, but are not limited to: Serum, plasma, sputum, seminal fluid, urine, other body fluids, and environmental samples such as ground water or waste water, soil extracts, air and pesticide residues.

The optical detection procedure or combination of optical detection procedures to be used will depend on the nature of the analytes, the separation device or matrix, as well as the structure and properties of the capture reagents. The separated complexes can be detected by one or a combination of optical techniques selected from adsorption, reflection, polarization, refraction, fluorescence, Raman spectra, SERS, resonance light scattering, grating-coupled surface plasmon resonance, using techniques described herein and as known in the art.

The Raman active labels are selected from a Raman-active dye, amino acid, nucleotide, or a combination thereof. Examples of Raman active amino acids suitable for incorporation into the Raman-active tag include arginine, methionine, cysteine, and combinations thereof. Examples of Raman-active nucleotides suitable for incorporation into the Raman-active tag include adenine, guanine and derivatives thereof. The Raman-active labels are small molecules that are highly active in producing a Raman signal and typically have a molecular weight of less than 1 kDa. Raman-active tags that meet these requirements include dyes (e.g., R6G, Tamra, Rox), amino acids (e.g., arginine, methionine, cysteine), nucleic acid bases (e.g., adenine, or guanine), or any combination thereof. Naturally occurring or synthetic compounds having the above-described characteristics, such as suitable molecular weight and Raman characteristics, can also be used. The Raman-active tags can be placed in any position along the molecular backbone and a single backbone can have more than one such tag. Raman signatures of the members of the set can be adjusted by changing the type, number and relative positions of the Raman-active tags along the backbone during synthesis of the molecular Raman codes.

The bound complexes including the Raman-active label is covered with a thin layer of metal, as described herein, to enhance Raman signals from the complex. The metal layer, being in close proximity to the analyte, will produce SERS signals and the complete solid support can be irradiated with a single light source while SERS signals are collected from the bound complexes, for example by SERS scanning. One or more SERS spectra obtained from a discrete site associates the capture reagent with the presence of a particular target analyte in the sample or identifies the capture reagent as having affinity (e.g., heretofore unknown) for a molecule or complex in the sample.

Antibodies and receptors are non-limiting examples of the capture reagents attached to the discrete locations on the solid support. Nucleic acids, phage-displayed peptides, nucleic acids, aptamers, ligands, lectins, and combinations thereof can also be used as capture reagents in the invention methods. The sample is not necessarily a body fluid, although it may be, but can comprise any mixed pool of analytes, including proteins, gluco-proteins, lipid proteins, nucleic acids, virus particles, polysaccharides, steroids, and combinations thereof. In one aspect, the sample comprises a pool of body fluid of patients known or suspected of having a particular disease.

The term "nucleic acid" is used broadly herein to mean a sequence of deoxyribonucleotides or ribonucleotides that are linked together by a phosphodiester bond. For convenience, the term "oligonucleotide" is used herein to refer to a polynucleotide that is used as a primer or a probe. Generally, an oligonucleotide useful as a probe or primer that selectively hybridizes to a selected nucleotide sequence is at least about 10 nucleotides in length, usually at least about 15 nucleotides in length, for example between about 15 and about 50 nucleotides in length.

A nucleic acid can be RNA or can be DNA, which can be a gene or a portion thereof, a cDNA, a synthetic polydeoxyribonucleic acid sequence, or the like, and can be single stranded or double stranded, as well as a DNA/RNA hybrid. In various embodiments, a polynucleotide, including an oligonucleotide (e.g., a probe or a primer) can contain nucleoside or nucleotide analogs, or a backbone bond other than a phosphodiester bond. In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide or oligonucleotide also can contain nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., *Nucl. Acids Res.* 22: 5220-5234 (1994); Jellinek et al., *Biochemistry* 34: 11363-11372 (1995); Pagratis et al., *Nature Biotechnol.* 15: 68-73 (1997).

The covalent bond linking the nucleotides of a nucleic acid generally is a phosphodiester bond. However, the covalent bond also can be any of numerous other bonds, including a thiodiester bond, a phosphorothioate bond, a peptide-like bond or any other bond known to those in the art as useful for linking nucleotides to produce synthetic polynucleotides (see, for example, Tam et al., *Nucl. Acids Res.* 22: 977-986 (1994); Ecker and Crooke, *BioTechnology* 13: 351360 (1995)). The incorporation of non-naturally occurring nucleotide analogs or bonds linking the nucleotides or analogs can be particularly useful where the polynucleotide is to be exposed to an environment that can contain a nucleolytic activity, including, for example, a tissue culture medium or upon administration to a living subject, since the modified polynucleotides can be less susceptible to degradation.

As used herein, the term "selective hybridization" or "selectively hybridize," refers to hybridization under moderately stringent or highly stringent conditions such that a nucleotide sequence preferentially associates with a selected nucleotide sequence over unrelated nucleotide sequences to a large enough extent to be useful in identifying the selected nucleotide sequence. It will be recognized that some amount of non-specific hybridization is unavoidable, but is acceptable provided that hybridization to a target nucleotide sequence is sufficiently selective such that it can be distinguished over the non-specific cross-hybridization, for example, at least about 2-fold more selective, generally at least about 3-fold more selective, usually at least about 5-fold more selective, and particularly at least about 10-fold more selective, as determined, for example, by an amount of labeled oligonucleotide that binds to target nucleic acid molecule as compared to a nucleic acid molecule other than the target molecule, particularly a substantially similar (i.e., homologous) nucleic acid molecule other than the target nucleic acid molecule. Conditions that allow for selective hybridization can be determined empirically, or can be estimated based, for example, on the relative GC:AT content of the hybridizing oligonucleotide and the sequence to which it is to hybridize, the length of the hybridizing oligonucleotide, and the number, if any, of mismatches between the oligonucleotide and sequence to which it is to hybridize (see, for example, Sambrook et al., "Molecular Cloning: A laboratory manual (Cold Spring Harbor Laboratory Press 1989)).

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42EC (moderate stringency conditions); and 0.1×SSC at about 68EC (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

As used herein, the term "antibody" is used in its broadest sense to include polyclonal and monoclonal antibodies, as well as antigen binding fragments of such antibodies. An antibody useful in a method of the invention, or an antigen binding fragment thereof, is characterized, for example, by having specific binding activity for an epitope of an analyte. Alternatively, as explained below, the analyte can be the probe antibody, particularly in embodiments of the invention methods wherein antibodies used as probes (e.g. active agents) are exposed to body fluids to screen a set of antibodies for utility as drug candidates.

The antibody, for example, includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains (see Huse et al., *Science* 246: 1275-1281 (1989)). These and other methods of making, for example, chimeric, humanized, CDR-grafted, single chain, and bifunctional antibodies are well known to those skilled in the art (Winter and Harris, *Immunol. Today* 14: 243-246, 1993; Ward et al., *Nature* 341: 544-546, 1989; Harlow and Lane, *Antibodies: A laboratory manual* (Cold Spring Harbor Laboratory Press, 1988); Hilyard et al., *Protein Engineering: A practical approach* (IRL Press 1992); Borrabeck, *Antibody Engineering*, 2d ed. (Oxford University Press 1995)). Monoclonal antibodies suitable for use as probes may also be obtained from a number of commercial sources. Such commercial antibodies are available against a wide variety of targets. Antibody probes can be conjugated to molecular backbones using standard chemistries, as discussed below.

The term "binds specifically" or "specific binding activity," when used in reference to an antibody means that an interaction of the antibody and a particular epitope has a dissociation constant of at least about $1\times10^{-6}$, generally at least about $1\times10^{-7}$, usually at least about $1\times10^{-8}$, and particularly at least about $1\times10^{-9}$ or $1\times10^{-10}$ or less. As such, Fab, F(ab')$_2$, Fd and Fv fragments of an antibody that retain specific binding activity for an epitope of an antigen, are included within the definition of an antibody.

In the context of the invention, the term "ligand" denotes a naturally occurring specific binding partner of a receptor, a synthetic specific-binding partner of a receptor, or an appropriate derivative of the natural or synthetic ligands. The determination and isolation of ligands is well known in the art (Lerner, *Trends Neurosci.* 17: 142-146, 1994). As one of skill in the art will recognize, a molecule (or macromolecular complex) can be both a receptor and a ligand. In general, the binding partner having a smaller molecular weight is referred to as the ligand and the binding partner having a greater molecular weight is referred to as a receptor.

In certain aspects, the invention pertains to methods for detecting an analyte in a sample. By "analyte" is meant any molecule or compound for which a probe can be found. An analyte can be in the solid, liquid, gaseous or vapor phase. By "gaseous or vapor phase analyte" is meant a molecule or compound that is present, for example, in the headspace of a liquid, in ambient air, in a breath sample, in a gas, or as a contaminant in any of the foregoing. It will be recognized that the physical state of the gas or vapor phase can be changed by pressure, temperature as well as by affecting surface tension of a liquid by the presence of or addition of salts etc.

The analyte can be a molecule found directly in a sample such as a body fluid from a host. The sample can be examined directly or can be pretreated to render the analyte more readily detectible. Furthermore, the analyte of interest can be determined by detecting an agent probative of the analyte of interest such as a specific binding pair member complementary to the analyte of interest, whose presence will be detected only when the analyte of interest is present in a sample. Thus, the agent probative of the analyte becomes the analyte that is detected in an assay. The body fluid can be, for example, urine, blood, plasma, serum, saliva, semen, stool, sputum, cerebral spinal fluid, tears, mucus, and the like.

As used herein, the term "colloid" refers to metal ions suspended in a liquid, usually water. Typical metals contemplated for use in invention metal colloids and to from nanoparticles include the transparent metals, for example, silver, gold, platinum, aluminum, and the like.

To enhance the Raman spectra produced by Raman-active substrates, a thin layer of a transparent metal, wherein the layer has a roughened surface, is deposited over the upper layer of the substrate and/or the bound complexes thereon. The roughness features are on the order of tens of nanometers; small, compared to the wavelength of the incident excitation radiation. The small size of the particles allows the excitation of the metal particle's surface plasmon to be localized on the particle. Metal roughness features at the metal surface can be developed in a number of ways; for example; vapor deposition of metal particles or application of metal colloids onto the upper layer of the biosensor. Since the surface electrons of the metal are confined to the particle, whose size is small, the plasmon excitation is also confined to the roughness feature. The resulting electromagnetic field of the plasmon is very intense, greatly enhancing the SERS signal as compared to a Raman signal.

It has been estimated that only 1 in 10 analyte molecules inelastically scatter in Raman Spectroscopy. However, in embodiments of the invention methods wherein the intensity of Raman signal from a scattering molecule is greatly enhanced under SERS conditions, low concentrations of a Raman-active analyte can be detected at concentrations as low as pico- and femto-molar. In some circumstances, the invention methods can be used to detect the presence of a single analyte molecule in a complex biological sample, such as blood serum, by depositing a thin layer of a transparent metal so as to be in contact with the bound complexes containing a Raman label. Gold, silver, copper and aluminum are the transparent metals most useful for this technique.

A roughened metal surface can be produced using one of several methods. The term "a thin metal layer" as used herein means a metal layer deposited by chemical vapor deposition over the bound complexes containing a Raman label. Alternatively, a thin metal layer means a layer of nanoparticles formed by subjecting a colloidal solution of metal cations to reducing conditions to form metal nanoparticles in situ. In some embodiments, the nanoparticles will contain the bound complexes. Alternatively, seed particles, for example attached to the Raman codes, can precipitate formation of the nanoparticles from a metal colloid solution. In this context, "thin" means having a thickness of about one-half the wavelength of the irradiating light source (usually a laser) to achieve the benefit of SERS, for example from about 15 nm to about 500 nm, such as about 100 nm to about 200 nm.

The "analytes", as the term is used herein, includes nucleic acids, proteins, peptides, lipids, carbohydrates, glycolipids, glycoproteins or any other potential target for which a specific probe can be prepared. As discussed above, antibody or aptamer probes can be incorporated into the invention active molecular Raman codes and used to identify any target for which an aptamer or antibody can be prepared. The presence of multiple analytes in a sample can be assayed simultaneously, since each member of a set can be distinguishably labeled and detected. Quantification of the analyte can be performed by standard techniques, well known in spectroscopic analysis. For example, the amount of analyte bound to an invention Raman probe construct can be determined by measuring the signal intensity produced and comparison to a calibration curve prepared from known amounts of similar Raman probe construct standards. Such quantification methods are well within the routine skill in the art.

A "substrate" as the term is used herein, includes such well known devices as chips or microtiter plates, may comprise a patterned surface containing individual discrete sites that can be treated as described herein bind to individual analytes or types of analytes. Alternatively, in embodiments wherein the probe Raman construct is attached to the substrate, a correlation between the location of an individual site on the array with the Raman code or probe located at that particular site can be made.

Array compositions may include at least a surface with a plurality of discrete substrate sites. The size of the array will depend on the end use of the array. Arrays containing from about 2 to many millions of different discrete substrate sites can be made. Generally, the array will comprise from two to as many as a billion or more such sites, depending on the size of the surface. Thus, very high density, high density, moderate density, low density or very low density arrays can be made. Some ranges for very high-density arrays are from about 10,000,000 to about 2,000,000,000 sites per array. High-density arrays range from about 100,000 to about 10,000,000 sites. Moderate density arrays range from about 10,000 to about 50,000 sites. Low-density arrays are generally less than 10,000 sites. Very low-density arrays are less than 1,000 sites.

The sites comprise a pattern, i.e. a regular design or configuration, or can be randomly distributed. A regular pattern of sites can be used such that the sites can be addressed in an X-Y coordinate plane. The surface of the substrate can be modified to allow attachment of analytes at individual sites. Thus, the surface of the substrate can be modified such that discrete sites are formed. In one embodiment, the surface of the substrate can be modified to contain wells, i.e. depressions in the surface of the substrate. This can be done using a variety of known techniques, including, but not limited to, photolithography, stamping techniques, molding techniques and microetching techniques. As will be appreciated by those in the art, the technique used will depend on the composition and shape of the substrate. Alternatively, the surface of the substrate can be modified to contain chemically derived sites that can be used to attach analytes or probes to discrete locations on the substrate. The addition of a pattern of chemical functional groups, such as amino groups, carboxy groups, oxo groups and thiol groups can be used to covalently attach molecules containing corresponding reactive functional groups or linker molecules.

Biological "analytes" may comprise naturally occurring proteins or fragments of naturally occurring proteins. Thus, for example, cellular extracts containing proteins, or random or directed digests of proteinaceous cellular extracts, can be used. In this way libraries of procaryotic and eukaryotic proteins can be made for screening the systems described herein. For example libraries of bacterial, fungal, viral, and mammalian proteins can be generated for screening purposes.

Methods for oligonucleotide synthesis are well known in the art and any such known method can be used. For example, oligonucleotides can be prepared using commercially available oligonucleotide synthesizers (e.g., Applied Biosystems, Foster City, Calif.). Nucleotide precursors attached to a variety of tags can be commercially obtained (e.g. Molecular Probes, Eugene, Oreg.) and incorporated into oligonucleotides or polynucleotides. Alternatively, nucleotide precursors can be purchased containing various reactive groups, such as biotin, diogoxigenin, sulfhydryl, amino or carboxyl groups. After oligonucleotide synthesis, tags can be attached using standard chemistries. Oligonucleotides of any desired sequence, with or without reactive groups for tag attachment, may also be purchased from a wide variety of sources (e.g., Midland Certified Reagents, Midland, Tex.).

The metal required for achieving a suitable SERS signal is inherent in the COIN, and a wide variety of Raman-active organic compounds can be incorporated into the particle. Indeed, a large number of unique Raman signatures can be created by employing nanoparticles containing Raman-active organic compounds of different structures, mixtures, and ratios. Thus, the methods described herein employing COINs are useful for the simultaneous detection of many analytes in a sample, resulting in rapid qualitative analysis of the contents of "profile" of a body fluid. In addition, since many COINs can be incorporated into a single nanoparticle, the SERS signal from a single COIN particle is strong relative to SERS signals obtained from Raman-active materials that do not contain the nanoparticles described herein as COINs. This situation results in increased sensitivity compared to Raman-techniques that do not utilize COINs.

COINs are readily prepared for use in the invention methods using standard metal colloid chemistry. The preparation of COINs also takes advantage of the ability of metals to adsorb organic compounds. Indeed, since Raman-active organic compounds are adsorbed onto the metal during formation of the metallic colloids, many Raman-active organic compounds can be incorporated into the COIN without requiring special attachment chemistry.

In general, the COINs used in the invention methods are prepared as follows. An aqueous solution is prepared containing suitable metal cations, a reducing agent, and at least one suitable Raman-active organic compound. The components of the solution are then subject to conditions that reduce the metallic cations to form neutral, colloidal metal particles. Since the formation of the metallic colloids occurs in the presence of a suitable Raman-active organic compound, the Raman-active organic compound is readily adsorbed onto the metal during colloid formation. This simple type of COIN is referred to as type I COIN. Type I COINs can typically be isolated by membrane filtration. In addition, COINs of different sizes can be enriched by centrifugation.

In alternative embodiments, the COINs can include a second metal different from the first metal, wherein the second metal forms a layer overlying the surface of the nanoparticle. To prepare this type of SERS-active nanoparticle, type I COINs are placed in an aqueous solution containing suitable second metal cations and a reducing agent. The components of the solution are then subject to conditions that reduce the second metallic cations so as to form a metallic layer overlying the surface of the nanoparticle. In certain embodiments, the second metal layer includes metals, such as, for example, silver, gold, platinum, aluminum, and the like. This type of COIN is referred to as type II COINs. Type II COINs can be isolated and or enriched in the same manner as type I COINs. Typically, type I and type II COINs are substantially spherical and range in size from about 20 nm to 60 nm. The size of the nanoparticle is selected to be about one-half the wavelength of light used to irradiate the COINs during detection.

Typically, organic compounds are attached to a layer of a second metal in type II COINs by covalently attaching organic compounds to the surface of the metal layer Covalent attachment of an organic layer to the metallic layer can be achieved in a variety ways well known to those skilled in the art, such as for example, through thiol-metal bonds. In alternative embodiments, the organic molecules attached to the metal layer can be crosslinked to form a molecular network.

The COIN(s) used in the invention methods can include cores containing magnetic materials, such as, for example, iron oxides, and the like. Magnetic COINs can be handled without centrifugation using commonly available magnetic particle handling systems. Indeed, magnetism can be used as a mechanism for separating biological targets attached to magnetic COIN particles tagged with particular biological probes.

As used herein, "Raman-active organic compound" refers to an organic molecule that produces a unique SERS signature in response to excitation by a laser. A variety of Raman-active organic compounds are contemplated for use as components in COINs. In certain embodiments, Raman-active organic compounds are polycyclic aromatic or heteroaromatic compounds. Typically the Raman-active organic compound has a molecular weight less than about 300 Daltons.

Additional, non-limiting examples of Raman-active organic compounds useful in COINs include TRIT (tetramethyl rhodamine isothiol), NBD (7-nitrobenz-2-oxa-1,3-diazole), Texas Red dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, 5-carboxy-2',4',5',7'-tetrachlorofluorescein, 5-carboxyfluorescein, 5-carboxy rhodamine, 6-carboxyrhodamine, 6-carboxytetramethyl amino phthalocyanines, azomethines, cyanines, xanthines, succinylfluoresceins, aminoacridine, and the like. These and other Raman-active organic compounds can be obtained from commercial sources (e.g., Molecular Probes, Eugene, Oreg.).

In certain embodiments, the Raman-active compound is adenine, adenine, 4-amino-pyrazolo(3,4-d)pyrimidine, 2-fluoroadenine, N6-benzolyadenine, kinetin, dimethyl-allyl-amino-adenine, zeatin, bromo-adenine, 8-aza-adenine, 8-azaguanine, 6-mercaptopurine, 4-amino-6-mercaptopyrazolo(3,4-d)pyrimidine, 8-mercaptoadenine, or 9-amino-acridine 4-amino-pyrazolo(3,4-d)pyrimidine, or 2-fluoroadenine. In one embodiment, the Raman-active compound is adenine.

When "fluorescent compounds" are incorporated into COINs, the fluorescent compounds can include, but are not limited to, dyes, intrinsically fluorescent proteins, lanthanide phosphors, and the like. Dyes useful for incorporation into COINs include, for example, rhodamine and derivatives, such as Texas Red, ROX (6-carboxy-X-rhodamine), rhodamine-NHS, and TAMRA (5/6-carboxytetramethyl rhodamine NHS); fluorescein and derivatives, such as 5-bromomethyl fluorescein and FAM (5'-carboxyfluorescein NHS), Lucifer Yellow, IAEDANS, 7-Me$_2$, N-coumarin-4-acetate, 7-OH-4-CH$_3$-coumarin-3-acetate, 7-NH$_2$-4CH$_3$-coumarin-3-acetate (AMCA), monobromobimane, pyrene trisulfonates, such as Cascade Blue, and monobromotrimethyl-ammoniobimane.

Exemplary uses for the methods described herein is to detect a target nucleic acid. Such a method is useful, for example, for detection of a single nucleotide polymorphism (SNP), for detection of infectious agents within a clinical sample, detection of an amplification product derived from genomic DNA or RNA or message RNA, or detection of a gene (cDNA) insert within a clone. For certain methods aimed at detection of a target polynucleotide, an oligonucleotide probe is synthesized using methods known in the art.

In the practice of the present invention, the Raman spectrometer can be part of a detection unit designed to detect and quantify Raman signals of the present invention by Raman spectroscopy. Methods for detection of Raman labeled analytes, for example nucleotides, using Raman spectroscopy are known in the art. (See, e.g., U.S. Pat. Nos. 5,306,403; 6,002,471; and 6,174,677). Variations on surface enhanced Raman spectroscopy (SERS), surface enhanced resonance Raman spectroscopy (SERRS) and coherent anti-Stokes Raman spectroscopy (CARS) have been disclosed.

A non-limiting example of a Raman detection unit is disclosed in U.S. Pat. No. 6,002,471. An excitation beam is generated by either a frequency doubled Nd:YAG laser at 532 nm wavelength or a frequency doubled Ti:sapphire laser at 365 nm wavelength. Pulsed laser beams or continuous laser beams can be used. The excitation beam passes through confocal optics and a microscope objective, and is focused onto the flow path and/or the flow-through cell. The Raman emission light is collected by the microscope objective and the confocal optics and is coupled to a monochromator for spectral dissociation. The confocal optics includes a combination of dichroic filters, barrier filters, confocal pinholes, lenses, and mirrors for reducing the background signal. Standard full field optics can be used as well as confocal optics. The Raman emission signal is detected by a Raman detector, that includes an avalanche photodiode interfaced with a computer for counting and digitization of the signal.

Another example of a Raman detection unit is disclosed in U.S. Pat. No. 5,306,403, including a Spex Model 1403 double-grating spectrophotometer with a gallium-arsenide photomultiplier tube (RCA Model C31034 or Burle Industries Model C3103402) operated in the single-photon counting mode. The excitation source includes a 514.5 nm line argon-ion laser from SpectraPhysics, Model 166, and a 647.1 nm line of a krypton-ion laser (Innova 70, Coherent).

Alternative excitation sources include a nitrogen laser (Laser Science Inc.) at 337 nm and a helium-cadmium laser (Liconox) at 325 nm (U.S. Pat. No. 6,174,677), a light emitting diode, an Nd:YLF laser, and/or various ions lasers and/or dye lasers. The excitation beam can be spectrally purified with a bandpass filter (Corion) and can be focused on the flow path and/or flow-through cell using a 6× objective lens (Newport, Model L6X). The objective lens can be used to both excite the Raman-active probe constructs and to collect the Raman signal, by using a holographic beam splitter (Kaiser Optical Systems, Inc., Model HB 647-26N18) to produce a right-angle geometry for the excitation beam and the emitted Raman signal. A holographic notch filter (Kaiser Optical Systems, Inc.) can be used to reduce Rayleigh scattered radiation. Alternative Raman detectors include an ISA HR-320 spectrograph equipped with a red-enhanced intensified charge-coupled device (RE-ICCD) detection system (Princeton Instruments). Other types of detectors can be used, such as Fourier-transform spectrographs (based on Michaelson interferometers), charged injection devices, photodiode arrays, InGaAs detectors, electron-multiplied CCD, intensified CCD and/or phototransistor arrays.

Any suitable form or configuration of Raman spectroscopy or related techniques known in the art can be used for detection of the target complex of the present invention, including but not limited to normal Raman scattering, resonance Raman scattering, surface enhanced Raman scattering, surface enhanced resonance Raman scattering, coherent anti-Stokes Raman spectroscopy (CARS), stimulated Raman scattering, inverse Raman spectroscopy, stimulated gain Raman spectroscopy, hyper-Raman scattering, molecular optical laser examiner (MOLE) or Raman microprobe or Raman microscopy or confocal Raman microspectrometry, three-dimensional or scanning Raman, Raman saturation spectroscopy, time resolved resonance Raman, Raman decoupling spectroscopy or UV-Raman microscopy.

In certain aspects of the invention, a system for detecting the target complex of the present invention includes an information processing system. An exemplary information processing system may incorporate a computer that includes a bus for communicating information and a processor for processing information. In one embodiment of the invention, the processor is selected from the Pentium® family of processors, including without limitation the Pentium® II family, the Pentium® III family and the Pentium® 4 family of processors available from Intel Corp. (Santa Clara, Calif.). In alternative embodiments of the invention, the processor can be a Celeron®, an Itanium®, or a Pentium Xeon® processor (Intel Corp., Santa Clara, Calif.). In various other embodiments of the invention, the processor can be based on Intel® architecture, such as Intel® IA-32 or Intel® IA-64 architecture. Alternatively, other processors can be used. The information processing and control system may further comprise any peripheral devices known in the art, such as memory, display, keyboard and/or other devices.

In particular examples, the detection unit can be operably coupled to the information processing system. Data from the detection unit can be processed by the processor and data stored in memory. Data on emission profiles for various Raman labels may also be stored in memory. The processor may compare the emission spectra from the target complexes in the flow path and/or flow-through cell to identify the Raman-active moiety in complexed with the target analyte or the capture reagent. The information processing system may also perform standard procedures such as subtraction of background signals or comparison of signals from different samples.

While certain methods of the present invention can be performed under the control of a programmed processor, in alternative embodiments of the invention, the methods can be fully or partially implemented by any programmable or hard-coded logic, such as Field Programmable Gate Arrays (FP- GAs), TTL logic, or Application Specific Integrated Circuits (ASICs). Additionally, the disclosed methods can be performed by any combination of programmed general purpose computer components and/or custom hardware components.

Following the data gathering operation, the data will typically be reported to a data analysis operation. To facilitate the analysis operation, the data obtained by the detection unit will typically be analyzed using a digital computer such as that described above. Typically, the computer will be appropriately programmed for receipt and storage of the data from the detection unit as well as for analysis and reporting of the data gathered.

In certain embodiments of the invention, custom designed software packages can be used to analyze the data obtained from the detection unit. In alternative embodiments of the invention, data analysis can be performed using an information processing system and publicly available software packages.

Exemplary Raman labels are provided below in Table 1.

TABLE 1

Raman labels selection

| Abbreviation | Name | Structure |
|---|---|---|
| AAD (AA) | 8-Aza-Adenine | 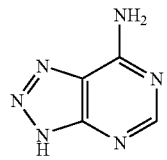 |
| BZA (BA) | N-Benzoyladenine | 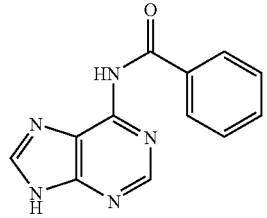 |
| APP | 4-Amino-pyrazolo[3,4-d]pyrimidine | 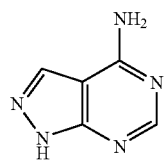 |
| ZEN | Zeatin | 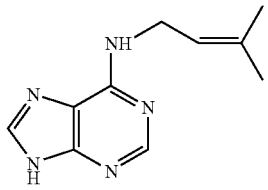 |
| MBL | Methylene Blue | 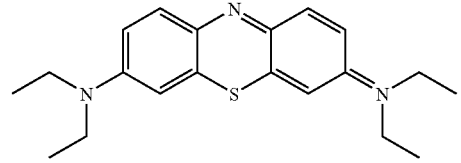 |
| AMA (AM) | 9-Amino-acridine | 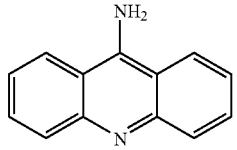 |

TABLE 1-continued
Raman labels selection
| Abbreviation | Name | Structure |
|---|---|---|
| EBR | Ethidium Bromide | 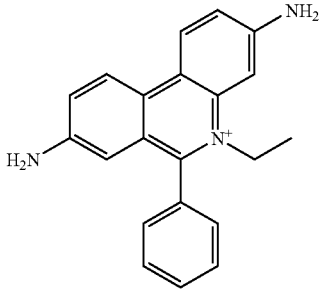 |
| BMB | Bismarck Brown Y | 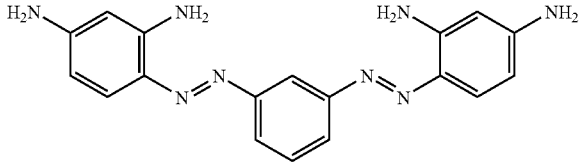 |
| THN | Thionin acetate | 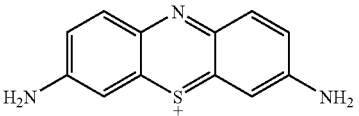 |
| DAH | 3,6-Diaminoacridine | 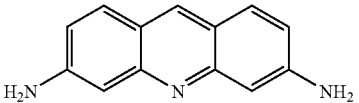 |
| AIC | 4-Amino-5-imidazole-carboxamide hydrochloride | 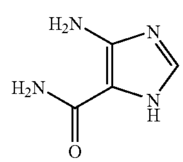 |
| DII | 1,3-Diiminoisoindoline | 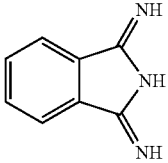 |
| R6G | Rhodamine 6G | 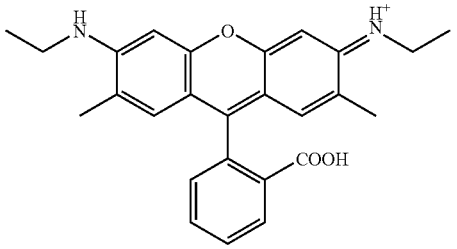 |

TABLE 1-continued

Raman labels selection

| Abbreviation | Name | Structure |
|---|---|---|
| CRV | Crystal Violet | 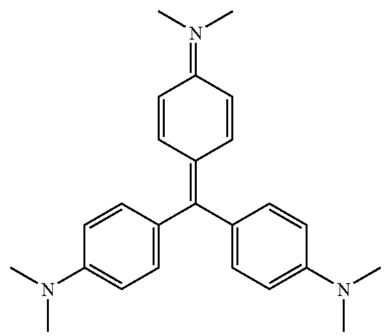 |
| BFU | Basic Fuchsin | 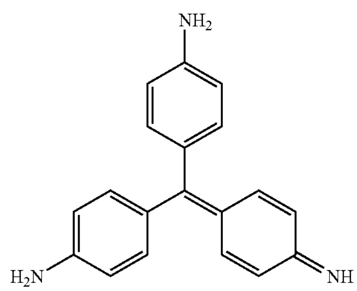 |
| NBA | N-Benzyl-aminopurine | 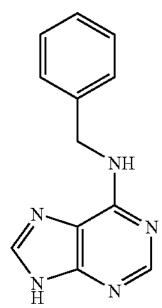 |
| MBI | 2-Mercapto-benzimidazole (MBI) | 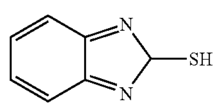 |
| CYP | 6-Cyanopurine | 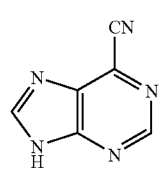 |

TABLE 1-continued

Raman labels selection

| Abbreviation | Name | Structure |
|---|---|---|
| ANB | Aniline Blue diammonium salt | 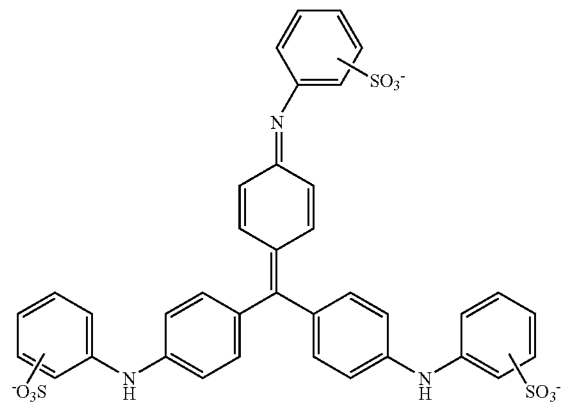 |
| ACA | N-[(3-(Anilinomethylene)-2-chloro-1-cyclohexen-1-yl)methylene]aniline monohydrochloride | 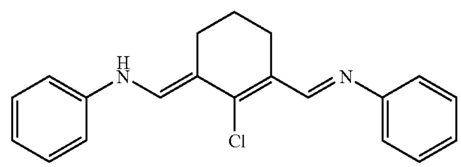 |
| ATT | O-(7-Azabenzotriazol-1-yl)-N,N,N',N'-tetramethyluronium hexafluorophosphate | 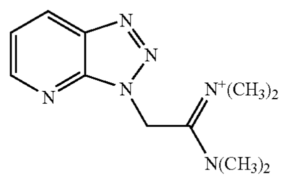 |
| AMF | 9-Aminofluorene hydrochloride | 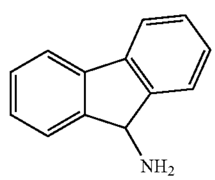 |
| BBL | Basic Blue | 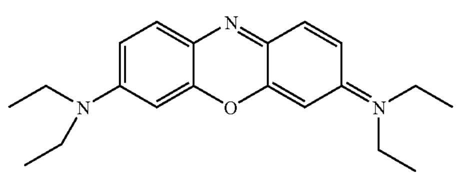 |
| DDA | 1,8-Diamino-4,5-dihydroxyanthraquinone | 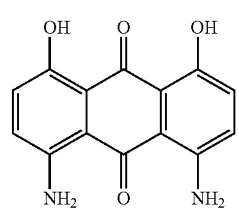 |
| PFV | Proflavine hemisulfate salt hydrate | 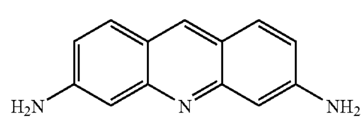 |

TABLE 1-continued

Raman labels selection

| Abbreviation | Name | Structure |
| --- | --- | --- |
| VRA | Variamine Blue RT Salt | 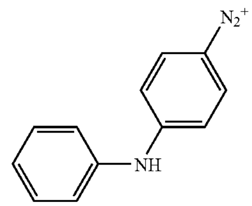 |
| ABZ | 2-Amino-benzothiazole | 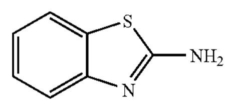 |
| MEL | Melamine | 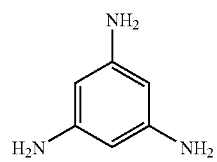 |
| PPN | 3-(3-Pyridylmethylamino)propionitrile | 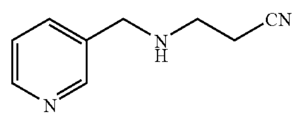 |
| SSD | Silver(I) sulfadiazine | 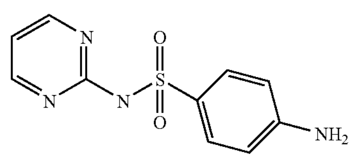 |
| AMPT | 4-Amino6-Mercaptopyrazolo[3,4-d]pyrimidine | 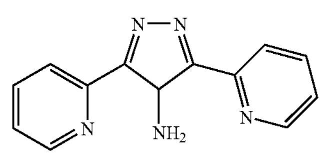 |
| APU | 2-Am-Purine | 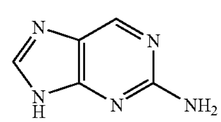 |
| ATH | Adenine Thiol | 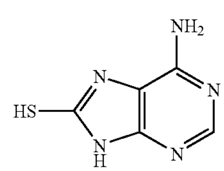 |
| FAD | F-Adenine | 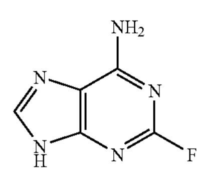 |

TABLE 1-continued

Raman labels selection

| Abbreviation | Name | Structure |
|---|---|---|
| MCP | 6-Mercaptopurine | 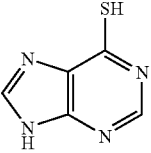 |
| AMP | 4-Amino-6-mercaptopyrazolo[3,4-d]pyrimidine | 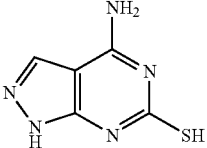 |
| R110 | Rhodamine 110 | 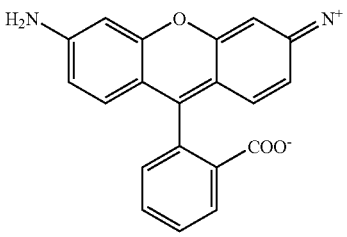 |
| DAB | 4-([4-(Dimethylamino)phenyl]azo)benzoic acid | 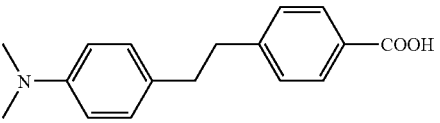 |

Although the invention has been described with reference to the above example, it will be understood that modifications and variations are encompassed within the spirit and scope of the invention. Accordingly, the invention is limited only by the following claims.

What is claimed is:

1. A reagent comprising:
   a) a first specific binding member;
   b) a second specific binding member that specifically binds to the first specific binding member, wherein the second specific binding member comprises a seed particle suitable for catalyzing the formation of a surface enhanced Raman scattering (SERS) substrate, the SERS substrate is suitable to be activated to provide a SERS effect and wherein neither the first nor the second specific binding members have Raman labels attached thereto; and
   c) a capture reagent bound to a solid substrate, wherein the capture reagent comprises a Raman label, and a target analyte bound to the capture reagent and the first specific binding member, thereby forming a biological target complex.

2. The reagent of claim 1, wherein the SERS substrate formed from the seed particle comprises a silver, gold or copper stain to achieve a SERS effect when irradiated.

3. The reagent of claim 1, wherein the target analyte is a DNA, RNA, polypeptide, antibody, antigen, carbohydrate or small molecule.

4. The reagent of claim 1, wherein the capture reagent is a DNA, RNA, polypeptide, antibody, antigen, carbohydrate or small molecule.

5. The reagent of claim 1, wherein the first or second specific binding member is a DNA, RNA, antibody, antigen, polypeptide or carbohydrate.

6. The reagent of claim 5, wherein one of the first or second specific binding member is biotin.

7. The reagent of claim 5, wherein one of the first or second binding member is avidin.

8. The reagent of claim 1, wherein the Raman label is a small molecule having a molecular weight of less than 400.

9. The reagent of claim 1, wherein the seed particle is selected from the group consisting of gold, Ag, Cu, Pt, Ag/Au, Pt/Au, Cu/Au coreshell and alloy particles.

10. The reagent of claim 1, wherein the target analyte further comprises an ancillary specific binding member.

11. The reagent of claim 1, wherein the target analyte and first specific binding member are associated by direct binding.

12. The reagent of claim 1, wherein the target analyte and first specific binding member are associated by indirect binding.

13. The reagent of claim 11, wherein the indirect binding is by binding through an intermediary molecule.

14. The reagent of claim 13, wherein the intermediary molecule is an antibody functionally associated with the first specific binding member.

15. A method comprising:
   a) providing a target analyte bound to a first specific binding member;
   b) providing a capture reagent bound to a solid substrate, wherein the capture reagent comprises a Raman label;

c) contacting the target analyte of a) with the capture reagent of b) under conditions suitable for forming a target analyte-capture reagent complex;

d) contacting, prior to, concurrently with, or subsequent to c) the first specific binding partner with a second specific binding member functionally associated with a seed particle suitable for associating with a SERS substrate, wherein the first specific binding member binds to the second specific binding member and wherein neither the first nor the second specific binding members have Raman labels attached; and e) contacting the target analyte-capture reagent complex with electromagnetic radiation suitable for detecting a specific property associated with the analyte capture reagent complex by Raman spectroscopy.

16. The method of claim 15, wherein the seed particle is selected from the group consisting of gold, Ag, Cu, Pt, Ag/Au, Pt/Au, Cu/Au coreshell and alloy particles.

17. The method of claim 15, wherein the target analyte and first specific binding member are associated by indirect binding.

18. A method comprising:

a) providing a target analyte bound to a first specific binding member;

b) providing a capture reagent bound to a solid substrate;

c) contacting the target analyte of a) with the capture reagent of b) under conditions suitable for forming a target analyte-capture reagent complex;

d) contacting, prior to, concurrently with, or subsequent to c) the first specific binding partner with a second specific binding member functionally associated with a seed particle suitable for associating with a SERS substrate, wherein the first specific binding member binds to the second specific binding member and wherein neither the first nor the second specific binding members have Raman libels attached;

e) contacting the SERS substrate with a Raman label; and f) contacting the target analyte-capture reagent complex with electromagnetic radiation suitable for detecting a specific property associated with the analyte-capture reagent complex by Raman spectroscopy.

19. The method of claim 18, wherein the seed particle is selected from the group consisting of gold, Ag, Cu, Pt, Ag/Au, Pt/Au, Cu/Au coreshell and alloy particles.

20. The method of claim 18, wherein the target analyte and first specific binding member are associated by indirect binding.

21. A test kit comprising:

a) a container comprising at least one first specific binding member suitable for attachment to a target analyte;

b) a container comprising at least one second specific binding member that binds to the first specific binding member, wherein the second specific binding member comprises a seed particle suitable for catalyzing the formation of a surface enhanced Raman scattering (SERS) substrate, wherein the SERS substrate can be activated to provide a SERS effect and wherein neither the first nor the second specific binding members have Raman labels attached;

c) a composition comprising a solid substrate comprising an array of capture reagents, a plurality of which comprise a Raman label.

22. The kit of claim 21, wherein the first or second specific binding member is a DNA, RNA, antibody, antigen, polypeptide or carbohydrate.

23. The kit of claim 21, wherein the first or second specific binding member is biotin.

24. The kit of claim 21, wherein the first or second binding member is avidin.

25. The kit of claim 21, wherein the Raman label is a small molecule having a molecular weight less than 400.

26. The kit of claim 21, wherein the seed particle is selected from the group consisting of gold, Ag, Cu, Pt, Ag/Au, Pt/Au, Cu/Au coreshell and alloy particles.

* * * * *